US012781288B1

(12) United States Patent
Kubicek-Sutherland et al.

(10) Patent No.: US 12,781,288 B1
(45) Date of Patent: Nov. 3, 2026

(54) COMPOSITIONS AND METHODS FOR DETECTING CORONAVIRUS

(71) Applicant: Triad National Security, LLC, Los Alamos, NM (US)

(72) Inventors: Jessica Zofie Kubicek-Sutherland, Los Alamos, NM (US); Karina Yusim, Santa Fe, NM (US); James Patrick Theiler, Los Alamos, NM (US); Brian Thomas Foley, Los Alamos, CA (US); Zachary Ray Stromberg, Los Alamos, NM (US); Jason David Gans, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 793 days.

(21) Appl. No.: 18/170,935

(22) Filed: Feb. 17, 2023

(51) Int. Cl.

| | |
|---|---|
| ***C12Q 1/68*** | (2018.01) |
| ***C12Q 1/686*** | (2018.01) |
| ***C12Q 1/70*** | (2006.01) |

(52) U.S. Cl.
CPC ............. *C12Q 1/701* (2013.01); *C12Q 1/686* (2013.01); *C12Q 2600/16* (2013.01)

(58) Field of Classification Search
None
See application file for complete search history.

(56) References Cited

FOREIGN PATENT DOCUMENTS

| | | | | | |
|---|---|---|---|---|---|
| CN | 111235316 A | * | 6/2020 | ............. | C12Q 1/701 |
| CN | 113186226 A | * | 7/2021 | ............. | C12Q 1/701 |
| WO | WO-2021205453 A1 | * | 10/2021 | ........... | C12Q 1/6869 |

OTHER PUBLICATIONS

WIPO translation of CN-113186226-A (Year: 2021).*
Guo et al., "Fluorescent hybridization probes for nucleic acid detection," Anal. Bioanal. Chem 402(10): 3115-3125 (Year: 2012).*
WIPO translation of CN-111235316-A (Year: 2020).*
Ott et al., "Stability of SARS-CoV-2 RNA Nonsupplemented Saliva," Emerging Infectious Diseases, vol. 27, No. 4 (Year: 2021).*
Stromberg et al., "Fast Evaluation of Viral Emerging Risks (FEVER): A computational tool for biosurveillance, diagnostics, and mutation typing of emerging viral pathogens," *PLOS Glob Public Health* 2(2):e0000207, 2022 (21 pages).

* cited by examiner

*Primary Examiner* — M Franco G Salvoza
(74) *Attorney, Agent, or Firm* — Klarquist Sparkman, LLP

(57) ABSTRACT

Primers and probes for detection of coronavirus nucleic acids and methods of their use are provided. In some examples, the primers and probes can discriminate between variant coronavirus nucleic acids.

7 Claims, 6 Drawing Sheets

Specification includes a Sequence Listing.

FIG. 4A
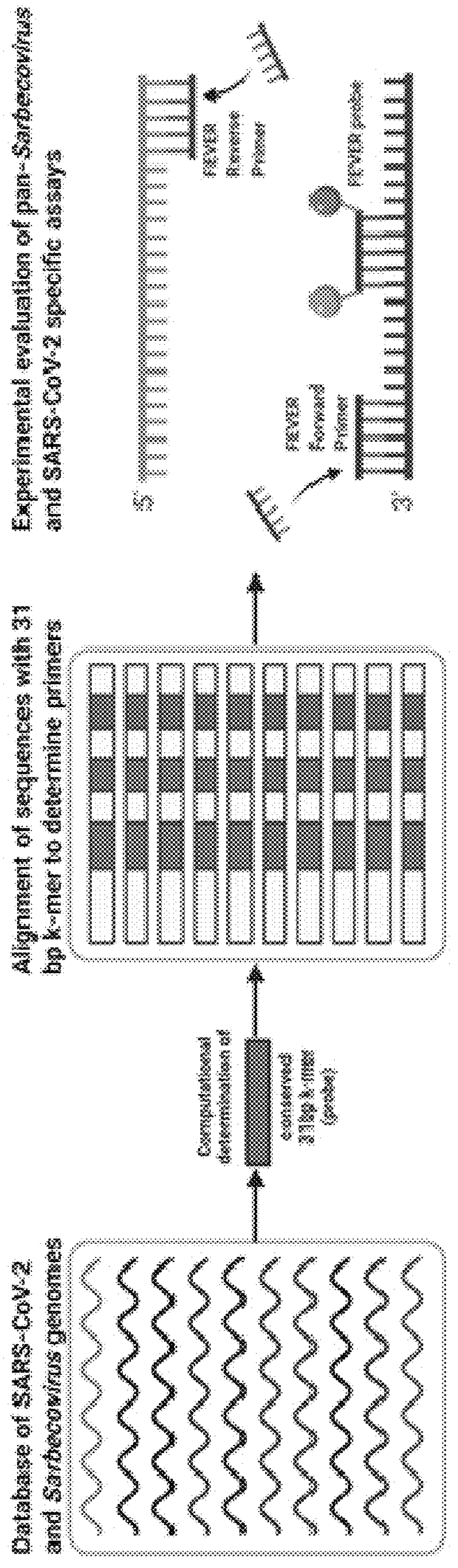
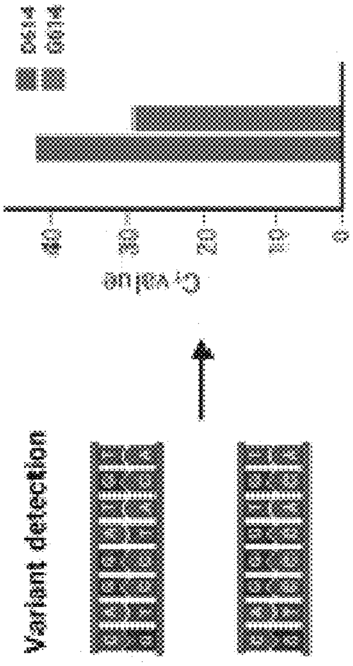
FIG. 4B
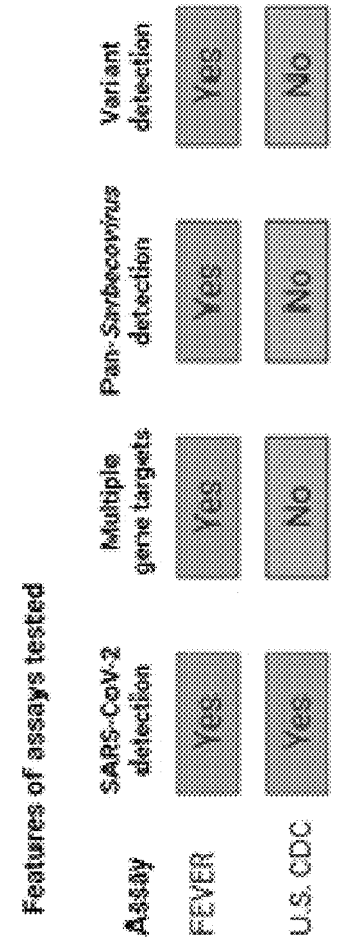
| Assay | SARS-CoV-2 detection | Multiple gene targets | Pan-*Sarbecovirus* detection | Variant detection |
|---|---|---|---|---|
| FEVER | Yes | Yes | Yes | Yes |
| U.S. CDC | Yes | No | No | No |
FIG. 4C

SEQUENCE LISTING

```
Sequence total quantity: 24
SEQ ID NO: 1            moltype = DNA  length = 25
FEATURE                 Location/Qualifiers
source                  1..25
                        mol_type = other DNA
                        organism = synthetic construct
SEQUENCE: 1
ctgcttacgg ttycgtccgt gttgc                                          25

SEQ ID NO: 2            moltype = DNA  length = 24
FEATURE                 Location/Qualifiers
source                  1..24
                        mol_type = other DNA
                        organism = synthetic construct
SEQUENCE: 2
actgagttgg acgtgtgttt tctc                                           24

SEQ ID NO: 3            moltype = DNA  length = 30
FEATURE                 Location/Qualifiers
source                  1..30
                        mol_type = other DNA
                        organism = synthetic construct
SEQUENCE: 3
```

-continued

```
ctctccatct tacctttcgg tcacacccgg                              30

SEQ ID NO: 4           moltype = DNA  length = 19
FEATURE                Location/Qualifiers
source                 1..19
                       mol_type = other DNA
                       organism = synthetic construct
SEQUENCE: 4
ccgacgacga ctactagcg                                          19

SEQ ID NO: 5           moltype = DNA  length = 23
FEATURE                Location/Qualifiers
source                 1..23
                       mol_type = other DNA
                       organism = synthetic construct
SEQUENCE: 5
gtttagacca gaagatcagg aac                                     23

SEQ ID NO: 6           moltype = DNA  length = 31
FEATURE                Location/Qualifiers
source                 1..31
                       mol_type = other DNA
                       organism = synthetic construct
SEQUENCE: 6
cgcacacaat cgaagcgcag taaggatggc t                            31

SEQ ID NO: 7           moltype = DNA  length = 23
FEATURE                Location/Qualifiers
source                 1..23
                       mol_type = other DNA
                       organism = synthetic construct
SEQUENCE: 7
atgaagtatt ttgtgaaaat agg                                     23

SEQ ID NO: 8           moltype = DNA  length = 20
FEATURE                Location/Qualifiers
source                 1..20
                       mol_type = other DNA
                       organism = synthetic construct
SEQUENCE: 8
cagctagaca cctagtcatg                                         20

SEQ ID NO: 9           moltype = DNA  length = 30
FEATURE                Location/Qualifiers
source                 1..30
                       mol_type = other DNA
                       organism = synthetic construct
SEQUENCE: 9
tctgaagcag tggaaaagca tgtggcacgt                              30

SEQ ID NO: 10          moltype = DNA  length = 24
FEATURE                Location/Qualifiers
source                 1..24
                       mol_type = other DNA
                       organism = synthetic construct
SEQUENCE: 10
tccctcaggg tttttcggct ttag                                    24

SEQ ID NO: 11          moltype = DNA  length = 25
FEATURE                Location/Qualifiers
source                 1..25
                       mol_type = other DNA
                       organism = synthetic construct
SEQUENCE: 11
gtttctgaga gagggtcaag tgcac                                   25

SEQ ID NO: 12          moltype = DNA  length = 31
FEATURE                Location/Qualifiers
source                 1..31
                       mol_type = other DNA
                       organism = synthetic construct
SEQUENCE: 12
tgcagcacca gctgtccaac ctgaagaaga a                            31

SEQ ID NO: 13          moltype = DNA  length = 27
FEATURE                Location/Qualifiers
source                 1..27
                       mol_type = other DNA
                       organism = synthetic construct
```

-continued

```
SEQUENCE: 13
ccaggaacaa atacttctaa ccaggtt                                   27

SEQ ID NO: 14          moltype = DNA  length = 24
FEATURE                Location/Qualifiers
source                 1..24
                       mol_type = other DNA
                       organism = synthetic construct
SEQUENCE: 14
gcatgaatag caacagggac ttct                                      24

SEQ ID NO: 15          moltype = DNA  length = 19
FEATURE                Location/Qualifiers
source                 1..19
                       mol_type = other DNA
                       organism = synthetic construct
SEQUENCE: 15
cagtgttccc acctacaag                                            19

SEQ ID NO: 16          moltype = DNA  length = 18
FEATURE                Location/Qualifiers
source                 1..18
                       mol_type = other DNA
                       organism = synthetic construct
SEQUENCE: 16
agtgttccca cttacaag                                             18

SEQ ID NO: 17          moltype = DNA  length = 24
FEATURE                Location/Qualifiers
source                 1..24
                       mol_type = other DNA
                       organism = synthetic construct
SEQUENCE: 17
tgcattctgc attgtgcaaa cttt                                      24

SEQ ID NO: 18          moltype = DNA  length = 30
FEATURE                Location/Qualifiers
source                 1..30
                       mol_type = other DNA
                       organism = synthetic construct
SEQUENCE: 18
ggaacaccat caacaaatat ttttctcact                                30

SEQ ID NO: 19          moltype = DNA  length = 19
FEATURE                Location/Qualifiers
source                 1..19
                       mol_type = other DNA
                       organism = synthetic construct
SEQUENCE: 19
cagtgttccc acctacaag                                            19

SEQ ID NO: 20          moltype = DNA  length = 18
FEATURE                Location/Qualifiers
source                 1..18
                       mol_type = other DNA
                       organism = synthetic construct
SEQUENCE: 20
agtgttccca cttacaag                                             18

SEQ ID NO: 21          moltype = DNA  length = 26
FEATURE                Location/Qualifiers
source                 1..26
                       mol_type = other DNA
                       organism = synthetic construct
SEQUENCE: 21
agtctggtga gtttaaattg gcttca                                    26

SEQ ID NO: 22          moltype = DNA  length = 27
FEATURE                Location/Qualifiers
source                 1..27
                       mol_type = other DNA
                       organism = synthetic construct
SEQUENCE: 22
acaatcacct tcttcttcat cctcatc                                   27

SEQ ID NO: 23          moltype = DNA  length = 16
FEATURE                Location/Qualifiers
source                 1..16
                       mol_type = other DNA
```

-continued

```
                        organism = synthetic construct
SEQUENCE: 23
tggagggtag aaagaa                                                 16

SEQ ID NO: 24           moltype = DNA  length = 16
FEATURE                 Location/Qualifiers
source                  1..16
                        mol_type = other DNA
                        organism = synthetic construct
SEQUENCE: 24
tggagggtaa aaagaa                                                 16
```

COMPOSITIONS AND METHODS FOR DETECTING CORONAVIRUS

ACKNOWLEDGMENT OF GOVERNMENT SUPPORT

This invention was made with government support under Contract No. 89233218CNA000001 awarded by the U.S. Department of Energy/National Nuclear Security Administration. The government has certain rights in the invention.

FIELD

This disclosure relates to probes and primers for detecting coronavirus nucleic acids and methods of using the probes and primers.

INCORPORATION OF ELECTRONIC SEQUENCE LISTING

The electronic sequence listing, submitted herewith as an XML file named 8472-105171-02.xml (21,835 bytes), created on Feb. 17, 2023, is herein incorporated by reference in its entirety.

BACKGROUND

In December 2019, an outbreak of a respiratory disease of an unknown cause was reported in Wuhan, China. The causative agent of this respiratory illness, known as COVID-19, was designated as severe acute respiratory syndrome coronavirus 2 (SARS-CoV-2). Transmission via airborne droplets is suspected and the virus could remain viable after aerosolized in artificial saliva for up to 90 minutes (Smither et al., *Emerging Microbes & Infections* 9:1415-1417, 2020).

The initial standard method for diagnosing COVID-19 was PCR detection of SARS-CoV-2 RNA sampled using a nasopharyngeal swab (NPS). However, due to the need for trained personnel, personnel protective equipment for personnel, the risk to healthcare workers collecting NPS, and the limited supply of critical materials such as swabs, it quickly became evident that alternative sample types that are non-invasive should be explored for sample testing. Therefore, other sample types such as oropharyngeal swabs, nasal swabs, urine, feces, and saliva have been explored for SARS-CoV-2 detection.

In addition to sample method, the detection by PCR must have target-specific primers and probes that remain sensitive and specific in spite of viral mutation. Current challenges with PCR assays for SARS-CoV-2 include suboptimal sensitivity.

SUMMARY

Provided herein are primers and probes for detection of coronaviruses and methods of their use. In some examples, the primers and probes can discriminate between SARS-CoV-2 and other SARS-like coronaviruses. In other examples, the primers and probes can discriminate between variant coronavirus nucleic acids (e.g., nucleic acids encoding variant spike proteins). Also provided is a method for developing primer and probe sets for genetically diverse viruses, designated Fast Evaluation of Viral Emerging Risks (FEVER).

In some aspects, probes capable of hybridizing to a coronavirus nucleic acid are provided. In some examples, the probes are between 15 and 40 nucleic acids in length and include a nucleic acid at least 90% identical to the nucleic acid sequence of any one of SEQ ID NO: 3, SEQ ID NO: 6, SEQ ID NO: 9, SEQ ID NO: 12, SEQ ID NO: 15, SEQ ID NO: 16, SEQ ID NO: 19, SEQ ID NO: 20, SEQ ID NO: 23, or SEQ ID NO: 24, or the reverse complement thereof. In some examples, the probe is labeled with a detectable label, such as a fluorophore and/or fluorescent quencher.

Also disclosed herein are primers capable of hybridizing to and directing amplification of a coronavirus nucleic acid. In some examples, the primers are between 15 and 40 nucleic acids in length and include a nucleic acid at least 90% identical to the nucleic acid sequence of any one of SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 13, SEQ ID NO: 14, SEQ ID NO: 17, SEQ ID NO: 18, SEQ ID NO: 21, or SEQ ID NO: 22, or the reverse complement thereof.

Disclosed herein are methods of detecting coronavirus nucleic acids in a sample (such as a biological sample or an environmental sample). In some aspects, the methods include contacting a sample with at least two primers and at least one probe, amplifying a coronavirus nucleic acid (for example, by polymerase chain reaction, such as real-time polymerase chain reaction), and detecting hybridization between the probe and a coronavirus nucleic acid in the sample. In some examples, the methods include contacting the sample with a set of primers and at least one probe, wherein the set comprises SEQ ID NOs: 1-3, SEQ ID NOs: 4-6, SEQ ID NOs: 7-9, SEQ ID NOs: 10-12, SEQ ID NOs: 13-16, SEQ ID NOs: 17-20, and/or SEQ ID NOs: 21-24.

Kits including the disclosed primers and probes are also provided. In some aspects, the kit includes at least one set of at least two primers and at least one probe. In some examples, the kits include at least one set of primers and at least one probe, wherein the set is selected from SEQ ID NOs: 1-3, SEQ ID NOs: 4-6, SEQ ID NOs: 7-9, SEQ ID NOs: 10-12, SEQ ID NOs: 13-16, SEQ ID NOs: 17-20, and/or SEQ ID NOS: 21-24.

The foregoing and other features of the disclosure will become more apparent from the following detailed description, which proceeds with reference to the accompanying figures.

BRIEF DESCRIPTION OF THE DRAWINGS

FIG. 1A) and FEVER SARS-CoV-2 (FEVER_5'UTR, FEVER_Env, FEVER_ORF1ab, and FEVER_Spike; FIG. 1B) RT-PCR assays in a saliva background. Inactivated SARS-CoV-2 isolate USA-WA1/2020 was spiked in human saliva and serial 10-fold diluted in saliva from $10^7$ to $10^2$ copies/mL.

Figure 1A:
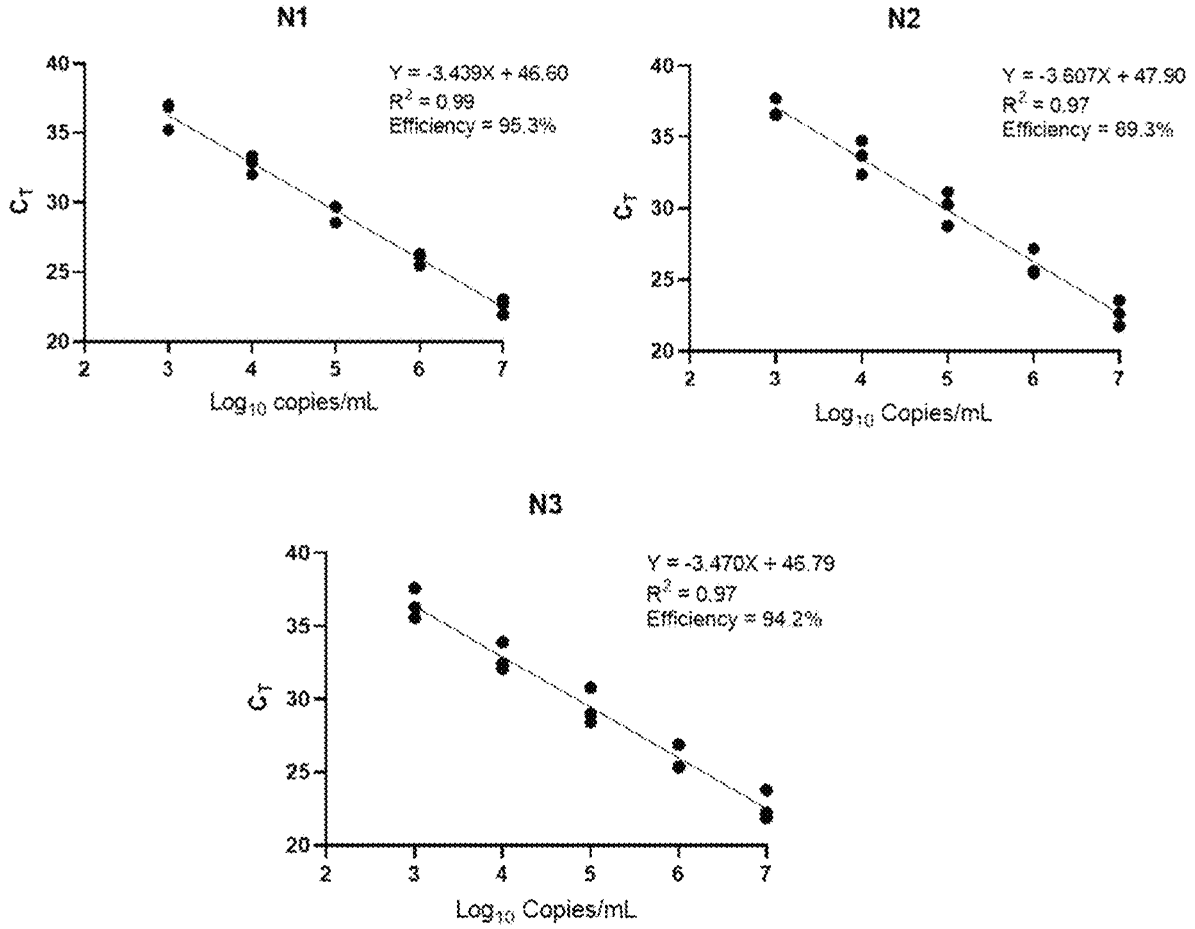
FIGS. 1A-1B show standard curves of U.S. CDC (N1, N2, and N3.

CDC and FEVER RT-PCR assays. Four biological replicates were performed for each assay.

FIGS. 4A-4C show schematics of the FEVER assay approach and comparison of features to the U.S. CDC SARS-CoV-2 assay. (FIG. 4A) Overview of compiling a database of SARS-CoV-2 and Sarbecovirus genome sequences to generate FEVER primer and probe sets. (FIG. 4B) Assays were designed to detect the D614G variant. (FIG. 4C) The tabulated features of the FEVER assays compared with the U.S. CDC SARS-CoV-2 assay.

DETAILED DESCRIPTION

In some aspects, probes capable of hybridizing to a coronavirus nucleic acid (such as a SARS-CoV-2 nucleic acid) are provided. In some examples, the probes are between 15 and 40 nucleic acids in length and include a nucleic acid at least 90% identical to (such as at least 90%, at least 91%, at least 92%, at least 93%, at least 94%, at least 95%, at least 96%, at least 97%, at least 98%, or at least 99% identical to) the nucleic acid sequence of any one of SEQ ID NO: 3, SEQ ID NO: 6, SEQ ID NO: 9, SEQ ID NO: 12, SEQ ID NO: 15, SEQ ID NO: 16, SEQ ID NO: 19, SEQ ID NO: 20, SEQ ID NO: 23, or SEQ ID NO: 24, or the reverse complement thereof. In other examples, the probe includes a nucleic acid including or consisting of the nucleic acid sequence of any one of SEQ ID NO: 3, SEQ ID NO: 6, SEQ ID NO: 9, SEQ ID NO: 12, SEQ ID NO: 15, SEQ ID NO: 16, SEQ ID NO: 19, SEQ ID NO: 20, SEQ ID NO: 23, or SEQ ID NO: 24, or the reverse complement thereof.

In some aspects, the probe is detectably labeled, either with an isotopic or non-isotopic label. Non-isotopic labels can, for instance, include a fluorescent or luminescent molecule, a hapten (for example, biotin), an enzyme or enzyme substrate, or a chemical. Such labels are chosen such that the hybridization of the probe with target nucleic acid (such as a coronavirus nucleic acid) can be detected. In some examples, the probe is labeled with a fluorophore. Non-limiting examples of suitable fluorophore labels include FAM, VIC, HEX, TET, or JOE. In some examples, the fluorophore is a donor fluorophore. In other examples, the fluorophore is an accepter fluorophore, such as a fluorescence quencher. In some examples, the probe includes both a donor fluorophore and an accepter/quencher fluorophore. Appropriate donor/acceptor fluorophore pairs can be selected by one skilled in the art. In particular examples, the probe may also include an internal quencher. In some examples, the probe is modified at the 3' end to prevent extension of the probe by a polymerase.

In particular examples, the acceptor fluorophore (such as a fluorescence quencher) is attached to the 3' end of the probe and the donor fluorophore is attached to the 5' end of the probe. In another particular example, the acceptor fluorophore (such as a fluorescence quencher) is attached to a modified nucleotide (such as a T, for example, an internal T) and the donor fluorophore is attached to the 5' end of the probe. In other examples, a donor fluorophore is attached to the 5' end of the probe, an acceptor fluorophore (such as a fluorescence quencher) is attached to the 3' end of the probe, and an acceptor fluorophore (such as a fluorescence quencher) is attached to a modified internal nucleotide of the probe. In a particular example, an acceptor fluorophore is a dark quencher, such as Dabcyl, QSY7 (Molecular Probes), QSY33 (Molecular Probes), BLACK HOLE QUENCHERS™ (Glen Research), ECLIPSE™ Dark Quencher (Epoch Biosciences), IOWA BLACK™ (Integrated DNA Technologies), or ZEN™ quencher (Integrated DNA Technologies).

Also disclosed herein are primers capable of hybridizing to and directing amplification of a coronavirus nucleic acid, such as a SARS-CoV-2 nucleic acid. In some examples, the primers are between 15 and 40 nucleic acids in length and include a nucleic acid at least 90% identical to (such as at least 90%, at least 91%, at least 92%, at least 93%, at least 94%, at least 95%, at least 96%, at least 97%, at least 98%, or at least 99% identical to) the nucleic acid sequence of any one of SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 13, SEQ ID NO: 14, SEQ ID NO: 17, SEQ ID NO: 18, SEQ ID NO: 21, or SEQ ID NO: 22, or the reverse complement thereof. In other examples, the primer includes or consists of the nucleic acid sequence of any one of SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 13, SEQ ID NO: 14, SEQ ID NO: 17, SEQ ID NO: 18, SEQ ID NO: 21, or SEQ ID NO: 22.

Also disclosed herein are method of detecting coronavirus nucleic acids in a sample (such as a biological sample or an environmental sample). In some aspects, the methods include contacting a sample with at least two primers (such as at least one forward primer and at least one reverse primer) and at least one probe, amplifying a coronavirus nucleic acid (for example, by polymerase chain reaction, such as real-time polymerase chain reaction), and detecting hybridization between at least one probe and a coronavirus nucleic acid in the sample. In some examples, the at least two primers are selected from SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 13, SEQ ID NO: 14, SEQ ID NO: 17, SEQ ID NO: 18, SEQ ID NO: 21, and SEQ ID NO: 22 and the at least one probe is selected from SEQ ID NO: 3, SEQ ID NO: 6, SEQ ID NO: 9, SEQ ID NO: 12, SEQ ID NO: 15, SEQ ID NO: 16, SEQ ID NO: 19, SEQ ID NO: 20, SEQ ID NO: 23, and SEQ ID NO: 24. In some examples, the methods include contacting the sample with a set of at least two primers and at least one probe, wherein the set comprises SEQ ID NOs: 1-3, SEQ ID NOs: 4-6, SEQ ID NOs: 7-9, SEQ ID NOs: 10-12, SEQ ID NOs: 13-16, SEQ ID NOs: 17-20, or SEQ ID NOs: 21-24.

In some aspects, the disclosed primers and probes detect SARS-CoV-2 nucleic acids (e.g., SEQ ID NOs: 1-12). In some examples, the disclosed primers and probes can detect all SARS-like coronaviruses, including SARS-CoV-2 (e.g., SEQ ID NOs: 1-6). In other examples, the disclosed primers and probes can detect SARS-CoV-2, but not other SARS-like coronaviruses (e.g., SEQ ID NOs: 7-12). In other examples, the primers and probes can discriminate between variant coronavirus nucleic acids (e.g., SEQ ID NOs: 13-24).

Any nucleic acid amplification method can be used to detect the presence of a coronavirus nucleic acid in the sample. In one specific, non-limiting example, polymerase chain reaction (PCR) is used to amplify the coronavirus nucleic acid. In other specific, non-limiting examples, real-time PCR, reverse transcription-polymerase chain reaction (RT-PCR), real-time reverse transcription-polymerase chain reaction (rRT-PCR), ligase chain reaction, or transcription-mediated amplification is used to amplify the coronavirus nucleic acid. In a specific example, the coronavirus nucleic acid is amplified by rRT-PCR. Techniques for nucleic acid amplification are known to those of ordinary skill in the art.

Appropriate samples include any environmental or biological samples, including clinical samples obtained from a human or animal subject. Suitable samples include but are not limited to, cells, tissues, bodily fluids (for example, blood, serum, urine, cerebrospinal fluid, bronchoalveolar lavage, tracheal aspirates or swabs, sputum, nasopharyngeal aspirates or swabs, oropharyngeal aspirates or swabs, saliva), eye swabs, cervical swabs, vaginal swabs, rectal swabs, and feces. In one non-limiting example, the sample is saliva.

Kits including the disclosed primers and probes are also provided. In some aspects, the kit includes at least one set of at least two primers and at least one probe. In some examples, the set comprises SEQ ID NOs: 1-3, SEQ ID NOs: 4-6, SEQ ID NOS: 7-9, SEQ ID NOs: 10-12, SEQ ID NOs: 13-16, SEQ ID NOs: 17-20, and/or SEQ ID NOs: 21-24. The kit may also include additional reagents, for example, for amplification and/or detection of coronavirus nucleic acids. In some examples, the kit includes one or more buffers, enzymes, and/or controls.

Embodiments of the probes, primers, methods and kits are further described in Stromberg et al., "Fast Evaluation of Viral Emerging Risks (FEVER): A computational tool for biosurveillance, diagnostics, and mutation typing of emerging viral pathogens," *PLOS Glob Public Health* 2 (2): e0000207, 2022, which is herein incorporated by reference in its entirety.

EXAMPLES

The following examples are provided to illustrate certain particular features and/or aspects. These examples should not be construed to limit the disclosure to the particular features or aspects described.

Example 1

Development of Primers and Probes

The goal of the probe design is to produce a short nucleotide sequence (called a K-mer, as it is of length K) that reacts with SARS-CoV-2 without also reacting to background material that may be present in the sample that is being tested. Other desirable properties of the probe, making it more effective in the experimental setup, include maintaining a high G/C content and reducing the "hairpin propensity" (the tendency of the probe string to fold over on itself) by ensuring that any self-complementary pairs of sub-strings in the probe are sufficiently short. The mathematical formalization of the problem is expressed in terms of a constrained optimization, with G/C content and length of self-complementary sub-strings taken as constraints, while maximizing coverage of the probe. A probe is said to "cover" a SARS-CoV-2 sequence if the probe's K-mer appears as a sub-sequence of that sequence. Thus, coverage is defined as the number of sequences in the database that are covered by the probe. "Exact" coverage corresponds to an exact match of probe and sub-sequence; "off-by-m" coverage corresponds to an approximate match in which all but m nucleotides agree. Given a database of SARS-CoV-2 sequences, the single probe design problem is to find a string of length K, subject to the constraints of G/C content and hairpin aversion, which covers as many SARS-CoV-2 sequences as possible. For the multi-probe design problem, we seek P probes instead of just one, and a P-probe design is said to cover a SARS-CoV-2 sequence if any one of the probes cover it.

Selection of K=31 was used because it was short enough that a single probe can cover a large fraction of the sequences in the SARS-CoV-2 database, but long enough that it will not accidentally cover potential background sequences.

The single-probe exact-match problem is the most straightforward. It works by extracting all K-mers from each of the sequences in the database, and then restricting consideration to those that exhibit a minimal G/C content and hairpin aversion. For every one of these K-mers, we count how many SARS-CoV-2 sequences are covered, being careful not to count a sequence twice even if the K-mer appears twice in it. Finally, we choose the K-mer with the largest count.

The single-probe off-by-m problem is somewhat more complicated in its implementation, but is conceptually similar to the exact-match problem. As with the exact-match problem, we restrict consideration to K-mers that are extracted from the SARS-CoV-2 sequences and that satisfy the G/C content and hairpin propensity constraints. In this case, however, a SARS-CoV-2 sequence is said to be covered by a candidate K-mer as long as there is some other K-length sub-sequence in that SARS-CoV-2 sequence whose Hamming distance to that candidate K-mer is m or less.

In practice, computing Hamming distances is much more expensive than identifying exact matches, and so we have set up a more sophisticated data structure to speed up the computation.

For the multi-probe design problem, we have explored a number of algorithms, and we have found to date that a naive approach produces probes of optimal or near-optimal quality. That naive approach is to design one probe at a time, with the first probe obtained from the single-probe design algorithm. At each step of the process, we eliminate from the SARS-CoV-2 database those sequences that are covered by the probes we have already. Then, using this truncated database, we again use the single-probe algorithm to find a probe that best covers the SARS-CoV-2 sequences that were missed by the probes we have so far. In this way we "chip away" at the SARS-CoV-2 database either until we have P probes or until we have finally covered the full database.

Real-time PCR primer and probe sets developed using this algorithm are shown in Table 1.

TABLE 1

PCR Primers and Probes

| Gene target | Primer or Probe Name | Sequence 5' to 3'* | SEQ ID NO: |
|---|---|---|---|
| 5'UTR-ORF1ab | CoV_FEVER_5'UTR_F | CTGCTTACGGTTYCGTCCGTGTTGC | 1 |
| | CoV_FEVER_5'UTR_R | ACTGAGTTGGACGTGTGTTTTCTC | 2 |
| | CoV_FEVER_5'UTR_P | FAM- | 3 |

TABLE 1-continued

PCR Primers and Probes

| Gene target | Primer or Probe Name | Sequence 5' to 3'* | SEQ ID NO: |
|---|---|---|---|
| | | CTCTCCATC/ZEN/TTACCTTTCGGTCACACCCGG-IABKFQ | |
| Envelope | CoV_FEVER_Env_F | CCGACGACGACTACTAGCG | 4 |
| | CoV_FEVER_Env_R | GTTTAGACCAGAAGATCAGGAAC | 5 |
| | CoV_FEVER_Env_P | FAM-CGCACACAA/ZEN/TCGAAGCGCAGTAAGGATGGCT-IABKFQ | 6 |
| ORF1ab | CoV_FEVER_ORF1ab_F | ATGAAGTATTTTGTGAAAATAGG | 7 |
| | CoV_FEVER_ORF1ab_R | CAGCTAGACACCTAGTCATG | 8 |
| | CoV_FEVER_ORF1ab_P | FAM-TCTGAAGCA/ZEN/GTGGAAAAGCATGTGGCACGT-IABKFQ | 9 |
| Spike | CoV_FEVER_Spike_F | TCCCTCAGGGTTTTTCGGCTTTAG | 10 |
| | CoV_FEVER_Spike_R | GTTTCTGAGAGAGGGTCAAGTGCAC | 11 |
| | CoV_FEVER_Spike_P | FAM-TGCAGCACC/ZEN/AGCTGTCCAACCTGAAGAAGAA-IABKFQ | 12 |
| Spike | 23403_F | CCAGGAACAAATACTTCTAACCAGGTT | 13 |
| | 23403_R | GCATGAATAGCAACAGGGACTTCT | 14 |
| | 23403_P1(Wuhan) | VIC-CAGTGTTCCCAC**C**TACAAG-NFQ | 15 |
| | 23403_P2(Italy) | FAM-AGTGTTCCCAC**T**TACAAG-NFQ | 16 |
| RdRp | 14408_F | TGCATTCTGCATTGTGCAAACTTT | 17 |
| | 14408_R | GGAACACCATCAACAAATATTTTTCTCACT | 18 |
| | 14408_P1(Wuhan) | VIC-CAGTGTTCCCAC**C**TACAAG-NFQ | 19 |
| | 14408_P2(Italy) | FAM-AGTGTTCCCAC**T**TACAAG-NFQ | 20 |
| nsp3 | 3037_F | AGTCTGGTGAGTTTAAATTGGCTTCA | 21 |
| | 3037_R | ACAATCACCTTCTTCTTCATCCTCATC | 22 |
| | 3037_P1(Wuhan) | VIC-TGGAGGGTA**G**AAAGAA-NFQ | 23 |
| | 3037_P2(Italy) | FAM-TGGAGGGTA**A**AAAGAA-NFQ | 24 |

*Bold nucleotide indicates position at which SNP is detected.

Example 2

FEVER Computational Tool

FEVER combines probes and primers generated to 1) broadly identify an entire group of viruses; 2) specifically detect a strain of interest; and 3) detect SNPs of importance to public health (FIGS. 4A-4C). The computational approach starts with a curated multiple sequence alignment. The FEVER algorithm does not however require sequences to be aligned in order to generate assays. The alignment was performed to avoid overrepresentation of any single isolate and ensure broad coverage of the pathogen of interest. First, we developed two alignments using the sequences available in GISAID: one with SARS-CoV-2 sequences and one with Sarbecovirus sequences. Next, our FEVER algorithm was applied to design probes using the Sarbecovirus alignment for biosurveillance and the SARS-CoV-2 alignment for diagnostics while also screening the results using parameters set for GC-content, hairpin propensity, and match recall to achieve high coverage as well as reagent manufacturing and performance compatibility. The FEVER algorithm identifies sets of probes that cover 100% of each multiple sequence alignment. Two pan-Sarbecoviruse (FEVER_5'UTR and FEVER_Env) and two SARS-CoV-2 (FEVER_ORFlab and FEVER_Spike) specific probes were needed to detect all input sequences. After the FEVER probes were designed, primers flanking the probe sites were designed using the PrimerDesign-M tool (Yoon et al., *Bioinformatics* 31 (9): 1472-1474, 2015; Brodin et al., *BMC Bioinformatics* 14 (1): 255, 2013) for use in RT-PCR assays (Table 1). Few variants were visually detected in the region of amplification of these primers and probes. Further, we designed TaqMan SNP Genotyping PCR probes and primers to detect the previously identified A23403G (D614G amino acid change) mutation in the spike gene (Korber et al., *Cell* 182:812-827, 2020). Mutations in the SARS-CoV-2 genome conferring a fitness advantage have been reported (Korber et al., *Cell* 182:812-827, 2020). However, rapid methods to characterize SARS-CoV-2 mutations are lacking. Together, the primers and probes for all three components (biosurveillance, diagnostics, and mutation typing) are referred to collectively as the FEVER assays.

Example 3

Evaluation of Detection of SARS-CoV-2 in Saliva Samples

Extraction. RNA extraction was performed using the QIAamp® Viral RNA Mini Kit (QIAGEN). A 140 µl portion of each sample was used for extraction, eluted with 60 µl of elution buffer, and 5 µl of the eluted template was used in PCR assays.

PCR detection of SARS-CoV-2. The FEVER assays were compared to the US CDC 2019-novel coronavirus (2019-nCoV) real-time RT-PCR diagnostic panel (Lu et al., Emerging Infectious Diseases 26:1654-1655, 2020). For the CDC assays, each 20 μl reaction consisted of 8.5 μl of water, 1.5 μl of combined primer and probe mix (IDT, 500 nM primer and 125 nM probe final concentrations), 5 μl of TaqPath 1-step RT-qPCR master mix (Thermo Fisher), and 5 μl of template. For the FEVER assays, each 20 μl reaction consisted of 8 μl of water, 2 μl of combined primer and probe mix (IDT, 500 nM primer and 250 nM probe final concentrations), 5 μl of TaqPath 1-step RT-qPCR master mix, and 5 μl of template. Thermocycling conditions using an ABI StepOne Plus were 25° C. for 2 min, 50° C. for 15 min, 95° C. for 2 min, followed by 45 cycles of 95° C. for 3 s and 55° C. for 30 s. Samples were considered positive for SARS-CoV-2 using the US CDC assay when both N1, N2, and the human RNase P were detected <40 $C_T$ and for the FEVER assay when the cycle threshold was <40 $C_T$.

Stability of SARS-CoV-2 in saliva. To determine the stability of SARS-CoV-2 in saliva, inactivated SARS-CoV-2 virus (BEI resources, NR-52286) was spiked in pooled human saliva as a reference saliva source. Samples were held for 0, 4, or 8 hours at room temperature or in a cooler on ice, extracted, and then PCR was performed.

Figure 1B:
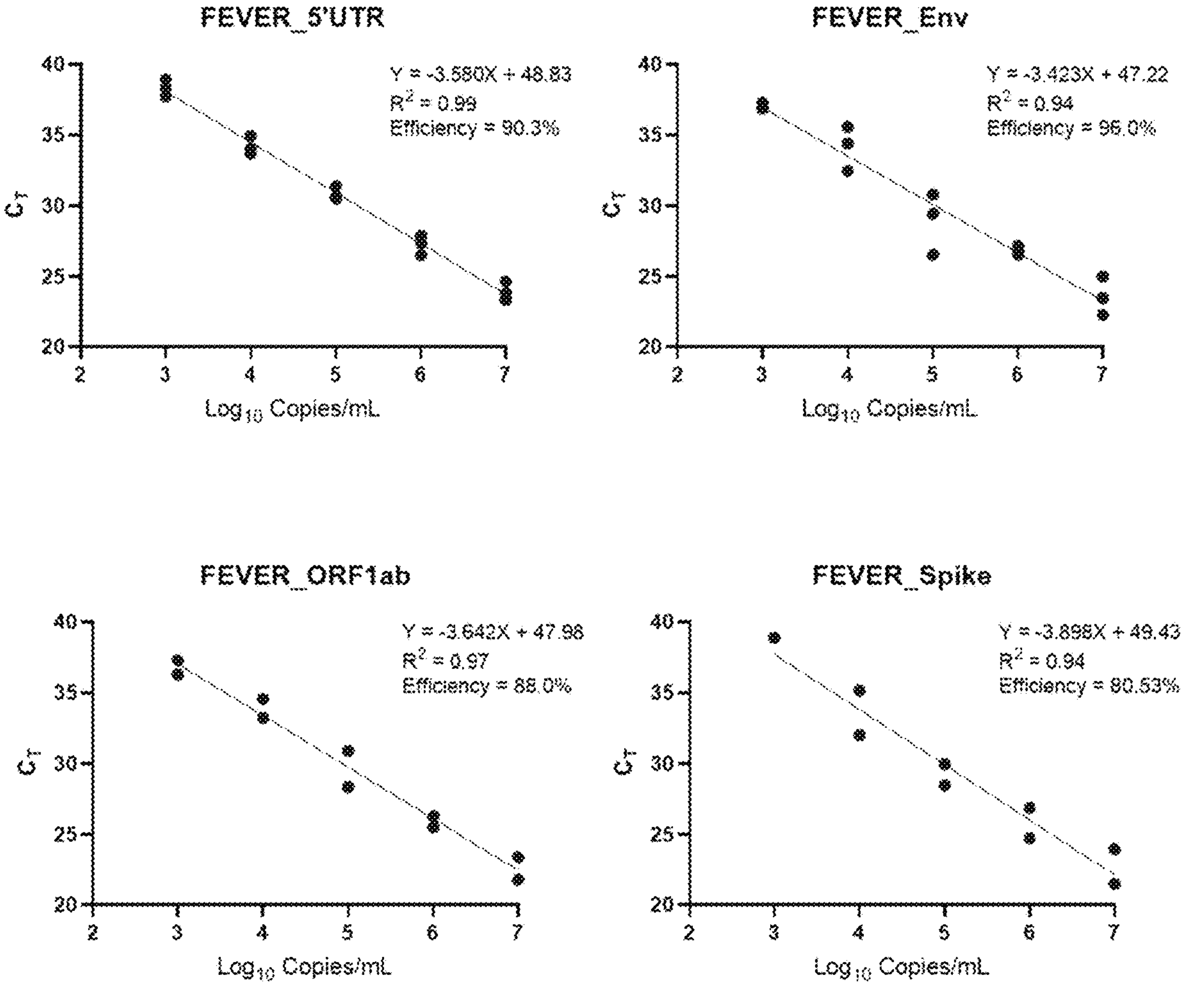

Limit of detection. The limit of detection (LOD) was determined by spiking SARS-CoV-2 inactivated virus (BEI resources, NR-52286) at $10^7$ copies/mL into saliva and performing 10-fold dilutions in saliva. Each concentration was tested using three biological replicates in triplicate (FIGS. 1A-1B).

PCR detection of common SNPs in SARS-CoV-2. A variant carrying the amino acid change D614G spike mutation became globally dominant, and the G614 variant has been suggested to have a fitness advance associated with higher viral loads (Korber et al., *Cell* 182:812-827, 2020). To assess the ability to detect common SNPs in SARS-CoV-2, custom TaqMan PCR assays were developed (Table 1). Each 20 μl reaction consisted of 9.5 μl of water, 0.5 μl of combined SNP genotyping primer and probe mix (Thermo Fisher, 900 nM primer and 200 nM probe final concentrations), 5 μl of TaqPath 1-step RT-qPCR master mix (Thermo Fisher), and 5 μl of template.

Pooling saliva. To evaluate the detection of SARS-CoV-2 in pooled saliva, a single positive sample at $10^7$ copies/mL or $10^4$ copies/mL was tested alone or in pools of 5, 10, 15, 20, 25, and 30 with negative saliva samples.

Statistical analyses. Data were analyzed with GraphPad Prism version 8.

Saliva storage in a cooler improved SARS-CoV-2 detection compared to room temperature. As shown in Table 2, storage in a cooler on ice improved sensitivity of the assay compared to storage for the same amount of time at room temperature.

TABLE 2

Effect of storage at room temperature or in a cooler on Ct values

| Target | 0 hour ($C_T$) | 4 h cooler ($C_T$) | 4 h room temperature ($C_T$) | 8 h cooler ($C_T$) | 8 h room temperature ($C_T$) |
|---|---|---|---|---|---|
| N1 (CDC) | 21.5 | 22.1 | 24.4 | 22.0 | 22.1 |
| N2 (CDC) | 22.0 | 23.3 | 24.3 | 21.8 | 24.9 |
| N3 (CDC) | 22.7 | 23.4 | 23.5 | 23.0 | 22.8 |
| RNase P (CDC) | 29.9 | 29.3 | 31.8 | 29.6 | 32.7 |
| CoV_FEVER_5'UTR | 24.2 | 24.7 | 25.2 | 24.8 | 24.9 |
| COV_FEVER_Env | 36.1 | 21.3 | 35.6 | 20.7 | 20.5 |
| COV_FEVER_ORF1ab | 27.9 | 27.8 | 28.4 | 26.4 | 28.1 |
| COV_FEVER_Spike | 25.1 | 24.4 | 28.5 | 25.0 | 28.3 |

Cycle threshold ($C_T$) values reported as a mean of three biological replicates.

Figure 2:
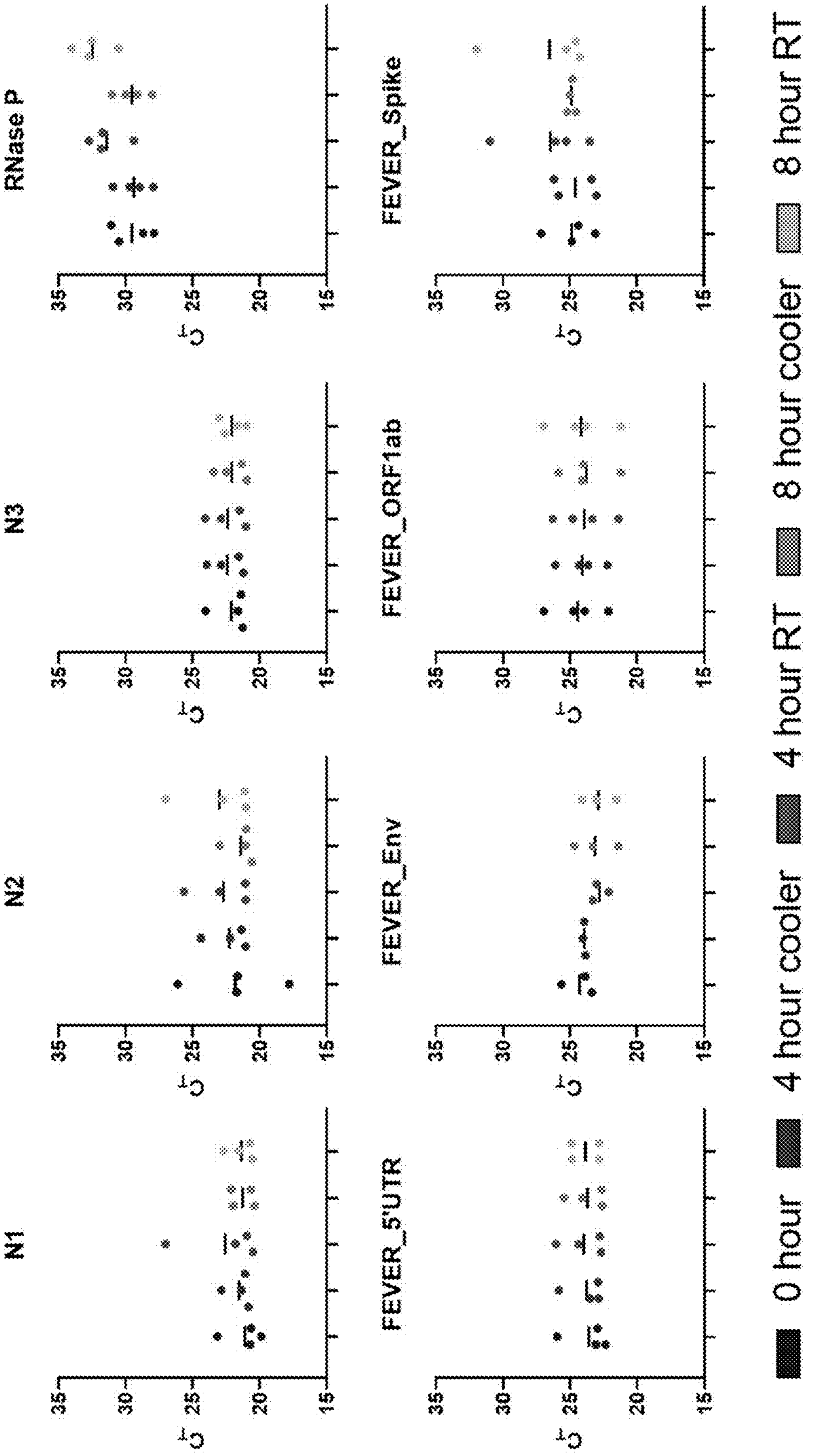
FIG. 2 shows evaluation of saliva storage conditions. Inactivated SARS-CoV-2 isolate USA-WA1/2020 was spiked in human saliva at $10^7$ copies/mL. Samples were stored for 0, 4, and 8 h in a cooler at 4° C. or at room temperature and then RNA was extracted. Extracted RNA was tested by U.S. CDC and FEVER RT-PCR assays. Four biological replicates were performed for each assay.

FEVER and CDC assays can detect as low as $10^3$ copies/mL of SARS-CoV-2 in saliva. Each assay was tested as a singleplex PCR assay with three biological replicates, and FEVER and CDC assays had similar LOD of assays of 1,000 copies/mL. The standard curves demonstrated correlation coefficients ($R^2$) between 0.97 and 0.99 and efficiency values between 89% to 95% (FIG. 2).

Figure 3A:
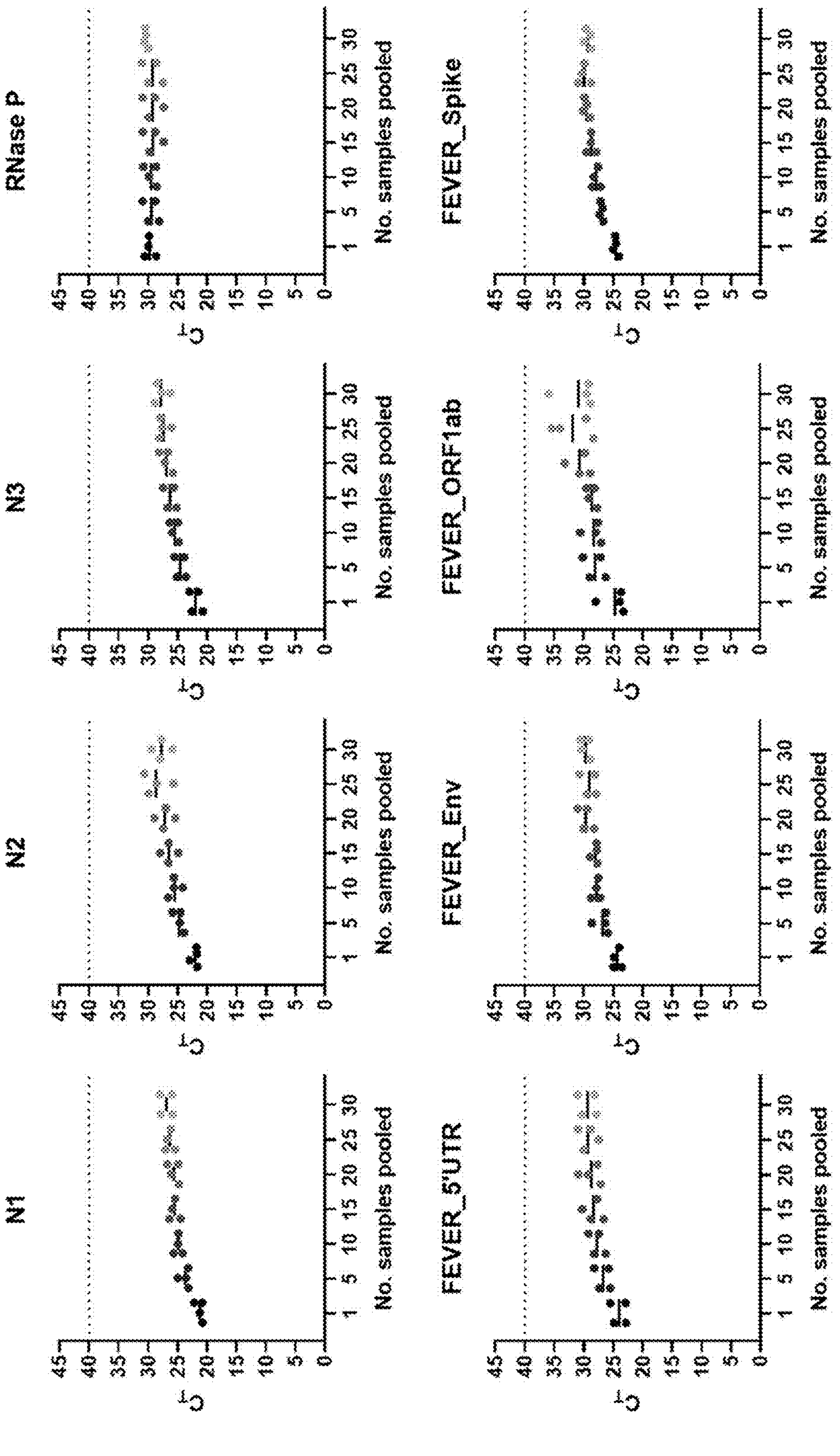
FIGS. 3A-3B show a comparison of cycle threshold ($C_T$) values between single positive and pooled positive samples. Inactivated SARS-CoV-2 isolate USA-WA1/2020 was spiked in human saliva at $10^7$ (FIG. 3A) or $10^4$ (FIG. 3B) copies/mL. A single positive spiked sample was tested alone or 50 μL of the positive sample was mixed with negative human saliva in pools of 5, 10, 15, 20, 25, and 30 total samples (50 μL each). Extracted RNA was tested by U.S.
Figure 3B:
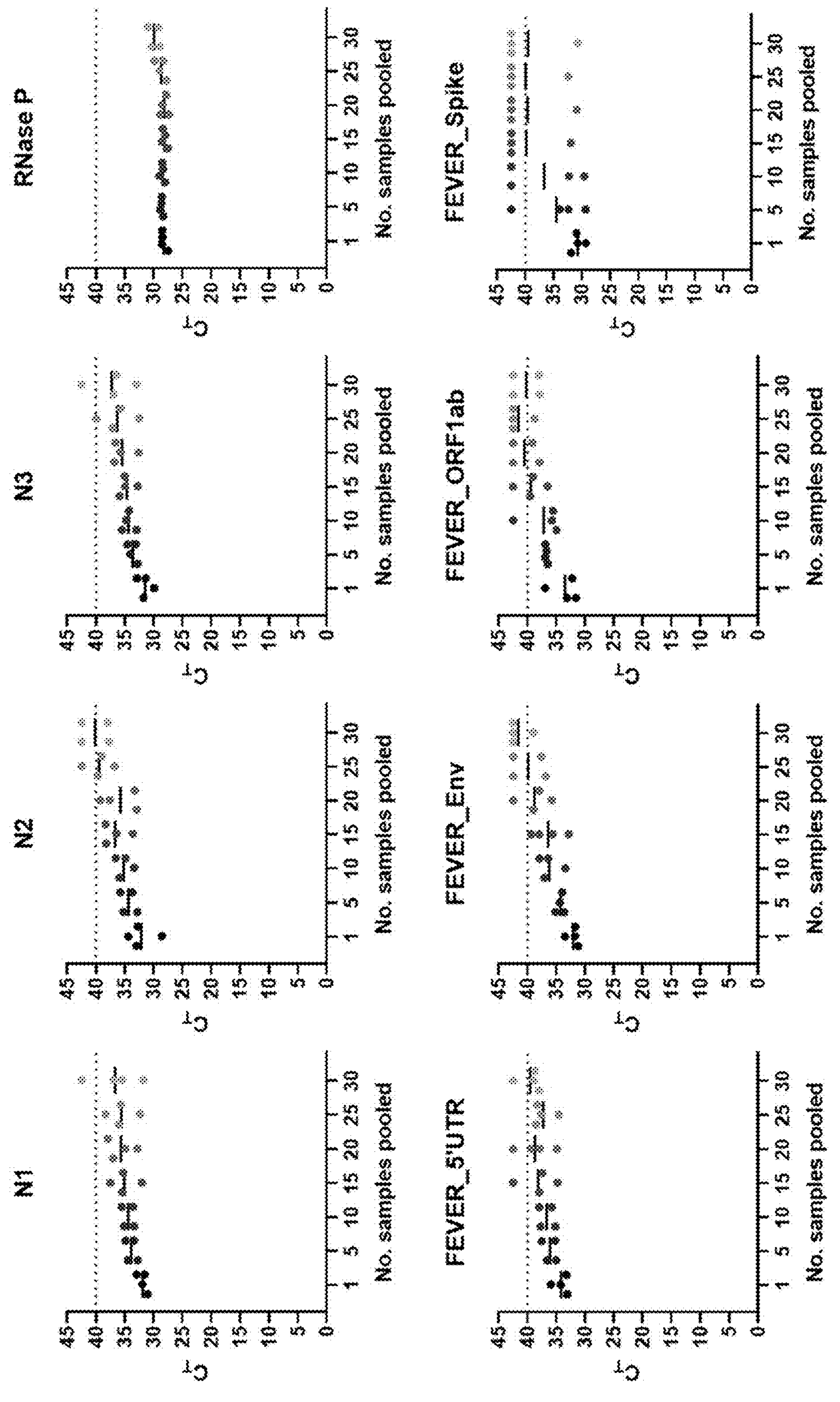

Pooling. To determine the effect of pooling on SARS-CoV-2 detection, we used a positive sample at $10^7$ copies/mL or $10^4$ copies/mL to mimic the average COVID patient and $10^4$ copies/mL to mimic a low-level infection and tested alone or in pools (5, 10, 15, 20, 25, and 30 samples) with negative saliva samples (FIGS. 3A-3B).

In view of the many possible aspects to which the principles of the disclosure may be applied, it should be recognized that the illustrated aspects are only examples and should not be taken as limiting the scope of the invention. Rather, the scope of the invention is defined by the following claims. We therefore claim as our invention all that comes within the scope and spirit of these claims.

We claim:

1. A method of detecting the presence of a coronavirus nucleic acid in a sample, comprising:

(a) contacting the sample with a set of primers and at least one probe, wherein the set of primers and probe(s) comprises:

(i) SEQ ID NOs: 1-3, (ii) SEQ ID NOs: 4-6, (iii) SEQ ID NOs: 7-9, (iv) SEQ ID NOs: 10-12, (v) SEQ ID NOs: 13-16, (vi) SEQ ID NOs: 17-20, and/or (vii) SEQ ID NOs: 21-24;

(b) amplifying a coronavirus nucleic acid if present in the sample; and (c) detecting hybridization between the coronavirus nucleic acid present in the sample and the probe.

2. The method of claim 1, wherein the sample is saliva, a nasopharyngeal swab, an oropharyngeal swab, a nasal swab, urine, or feces.

3. The method of claim 1, wherein the at least one probe in the set of primers and probe is detectably labeled.

4. The method of claim 3, wherein the detectable label is a fluorescent label, fluorophore, or fluorescence quencher.

5. The method of claim 1, wherein amplifying the coronavirus nucleic acid comprises polymerase chain reaction (PCR), reverse transcription-PCR, real-time PCR, or real-time reverse transcription-PCR.

6. The method of claim 1, wherein the coronavirus nucleic acid is a SARS-CoV-2 nucleic acid.

7. The method of claim 1, wherein the nucleic acid sequences of the set of primers and probe consist of SEQ ID NO: 4, SEQ ID NO: 5 and SEQ ID NO: 6.

* * * * *